(12) United States Patent
Ševčík

(10) Patent No.: US 7,246,938 B2
(45) Date of Patent: Jul. 24, 2007

(54) APPARATUS AND METHOD FOR MEASURING THE HEATING VALUE OF GASES

(75) Inventor: Jirí Ševčík, Praha (CZ)

(73) Assignees: RWE Transgas Net, S.R.O., Rraha (CZ); Jiri Sevcik, Prague (CZ)

( * ) Notice: Subject to any disclaimer, the term of this patent is extended or adjusted under 35 U.S.C. 154(b) by 126 days.

(21) Appl. No.: 10/533,171

(22) PCT Filed: Nov. 11, 2003

(86) PCT No.: PCT/CZ03/00065

§ 371 (c)(1),
(2), (4) Date: Apr. 29, 2005

(87) PCT Pub. No.: WO2004/048954

PCT Pub. Date: Jun. 10, 2004

(65) Prior Publication Data

US 2006/0007982 A1    Jan. 12, 2006

(30) Foreign Application Priority Data

Nov. 13, 2002   (CZ) .................................. 2002-3767

(51) Int. Cl.
*G01N 25/00* (2006.01)
*G01N 17/06* (2006.01)
*G01N 25/20* (2006.01)

(52) U.S. Cl. ............................ 374/36; 374/31; 374/10; 374/1; 374/148; 73/865.6

(58) Field of Classification Search ..................... None
See application file for complete search history.

(56) References Cited

U.S. PATENT DOCUMENTS

| | | | | | |
|---|---|---|---|---|---|
| 2,026,180 | A | * | 12/1935 | Keith | 374/37 |
| 3,718,437 | A | * | 2/1973 | Paloniemi | 422/51 |
| 4,306,451 | A | * | 12/1981 | Szonntagh | 374/36 |
| 4,720,196 | A | * | 1/1988 | Mondeil et al. | 374/37 |
| 4,761,744 | A | * | 8/1988 | Singh et al. | 700/274 |
| 4,869,597 | A | * | 9/1989 | Christopher | 374/37 |
| 5,759,862 | A | * | 6/1998 | Vander Heyden et al. | 436/147 |
| 5,882,115 | A | * | 3/1999 | Vander Heyden et al. | 374/37 |
| 5,988,875 | A | * | 11/1999 | Gershfeld et al. | 374/10 |
| 6,010,243 | A | * | 1/2000 | Hessler et al. | 374/1 |
| 6,371,147 | B1 | * | 4/2002 | Philippe | 137/6 |
| 2005/0190813 | A1 | * | 9/2005 | Schick | 374/10 |
| 2006/0123892 | A1 | * | 6/2006 | Brekelmans et al. | 73/61.76 |

* cited by examiner

*Primary Examiner*—Gail Verbitsky
(74) *Attorney, Agent, or Firm*—Notaro & Michalos

(57) ABSTRACT

A heating value meter for gases has an outer cylindrical mantle with an outer thermostatic heating apparatus and at least one inlet for introduction of air and at least one inlet for introduction of test or calibration gas. The outer mantle has an outer heating mantle and a bottom part containing an outer sensor of the outer thermostatic apparatus. A cylindrical measuring block is located coaxially inside the outer mantle and is equipped with an axially inserted internal sensor of an electrical remote thermometer of an internal thermostatic apparatus. The heating mantle, the outer sensor, an electrical heating block and an internal sensor, are interconnected via the outer and internal thermostatic apparatus and are adjusted for maintaining a constant temperature by regulation of the electrical input to the electrical heating block, or by the input to the heating mantle where, in addition, the measuring apparatus is connected by an electric lead to the electrical heating block.

11 Claims, 2 Drawing Sheets

APPARATUS AND METHOD FOR MEASURING THE HEATING VALUE OF GASES

TECHNICAL FIELD

The invention relates to a measurement of the heat of combustion of gases, or the heating value of gases, especially it concerns meters for determination of the heat of combustion of heating gases whose heating capacity may vary during delivery to the customers, and thus continuous monitoring is required. The invention relates to a metering method, too.

BACKGROUND ART

A great variety of instruments are used at the present time for measurement of the heat of combustion of gases. The so-called compensation meters that in principle compensate the differences in the heat of combustion of the test gas through the heat produced in a compensation source whose energy input is measured are often used for continuous measurement. In a number of these meters, an electrically heated block serves as the compensation source. In this case, the issue must be solved of attaining an equilibrium state between the input of heat from the compensation and test sources and the heat dissipation into the environment. A possible solution to this problem is described in a patent CH 593484 where the test and compensation heat sources are placed in the meter block that is connected to the cooling block by means of a heat-conducting element and the heat gradient between the measuring and cooling blocks is maintained constant and measured. The outer mantle around the measuring block is a part of the thermal insulation preventing heat dissipation into the environment along pathways other than that via the heat-conducting element. Such a measuring instrument is suitable for determining the heating capacity of a stable source placed in the measuring chamber but is less suited to continuous measurement of the heat of combustion of gases, where the gas passes through the measuring space and where it would be difficult to thermally insulate the measuring space. Another solution can be seen in a patent SU 1160294, where gases pass through the measuring chamber which is neighbouring to the compensation chamber and where the two chambers are interconnected by a heat-conducting material while the outer mantle of the meter is equipped with ribs for heat dissipation under which semiconductor thermo batteries are placed. This design is adapted for gas passage but it seems that this system combining controlled heat dissipation across thermo batteries and cooling ribs and thermal insulation of the remaining surface of the outer mantle, is rather complicated and it might be difficult to practically attain rapid and sufficiently sensitive regulation of heat dissipation. Further patents, SU 1286979, 1288567, 1390557, 1402894, 1420496, 1430849, 1430850, 1430851, 1492254 and 1492255, include attempts to compensate the above drawbacks of instruments of similar types by modifying the arrangement of the measuring and compensation chambers and by adding further heating blocks.

DISCLOSURE OF INVENTION

The drawbacks of the instruments described above are substantially reduced and precise measurement of the heating value of gases is attained by a relatively technically simple instrument when using apparatus for measuring the heating of gases according to the present invention comprising an outer mantle with thermostatically controlled heating and at least one inlet for air and one inlet for the test gas, and of a measuring block located inside the outer mantle, where the principle of this apparatus lies in the fact that the outer mantle is cylindrical and provided with a heating mantle on its outside surface, and that its bottom part contains an axially placed outer sensor of an electrical remote thermometer of the outer thermostatic apparatus, and the measuring block is also cylindrical, with an axially placed through-hole, it is placed coaxially inside the outer mantle and it is provided in the upper part with an axially-inserted heating block and in the bottom part with an axially-inserted internal sensor of an electrical remote thermometer of the internal thermostatic apparatus, while the heating mantle and the outer sensor and the electrical heating block and the internal sensor are interconnected via the internal and external thermostatic apparatus adjusted for maintaining a constant temperature by regulating the input of the electrical heating block or of the input of the heating mantle wherein the measuring apparatus of the electrical input is also connected to the electric lead of the electrical heating block. It could be advantageous when both the outer mantle and the measuring block of apparatus for measuring the heating of gases are made of a metallic material, with especial advantage of an alloy based on copper or aluminium. It is also advantageous when there is a gap between the outer surface of the measuring block and the internal surface of the outer mantle, wherein a width of the gap equals to 0.3 to 3.0 multiple of the outer diameter of the measuring block. It is also an advantage if the overall cross-section of the outlets of the flue gases equals 1.1 to 2.0 multiple of the overall cross-section area of the air inlets. It is further advantageous if there are at least two air inlets in the outer mantle and if they are directed at an angle and/or are diverging from the longitudinal axis of the measuring block. It is advantageous, too, if the electrical heating block and/or the internal sensor are placed closer to the circumference of the measuring block than to its axial through-hole. It is also advantageous if a cavity is created or a shielding body made of a thermally insulating material, is placed between the electrical heating block and/or the internal sensor, and the axial through-hole. Finally, it may be advantageous if the internal thermostatic apparatus is adjusted for regulation of the electrical input to the electrical heating block within a range from 5 to 50% of the heating input of the calibration gas being combusted in the meter. Another principle underlying the invention is the mode of operation of the meter, or a method for measuring the heating of gas, that involves first a calibration stage consisting of feeding a calibration gas with an exactly known heating capacity to the meter and of its combustion, followed by measurement of the temperature of the internal sensor and storage of the value in the memory of the measuring apparatus, and subsequently a measuring stage in which the test gas is introduced into the meter and combusted while the measuring apparatus measures the electrical input to the electrical heating block, the internal thermostatic apparatus maintains the measuring block temperature, measured at the internal sensor, at the same values as those obtained and stored in the memory during the calibration stage, and the value of the heat of combustion of the test gas is determined from the difference between the value of the heating capacity of the calibration gas and that of the electrical heating block, maintaining the temperature of the outer mantle at the constant value during the calibration and measuring stage. It is favourable to repeat the calibration stage every 30 to 300 minutes.

In this way a meter is obtained that is relatively simple and still reliably measures the heat of combustion of gases with a common precision of around 1%, or even better.

BRIEF DESCRIPTION OF DRAWINGS

Below, the invention is more closely explained and described on a preferred embodiment, with reference to the accompanying drawings in which.

MODES FOR CARRYING OUT THE INVENTION

Figure 1:
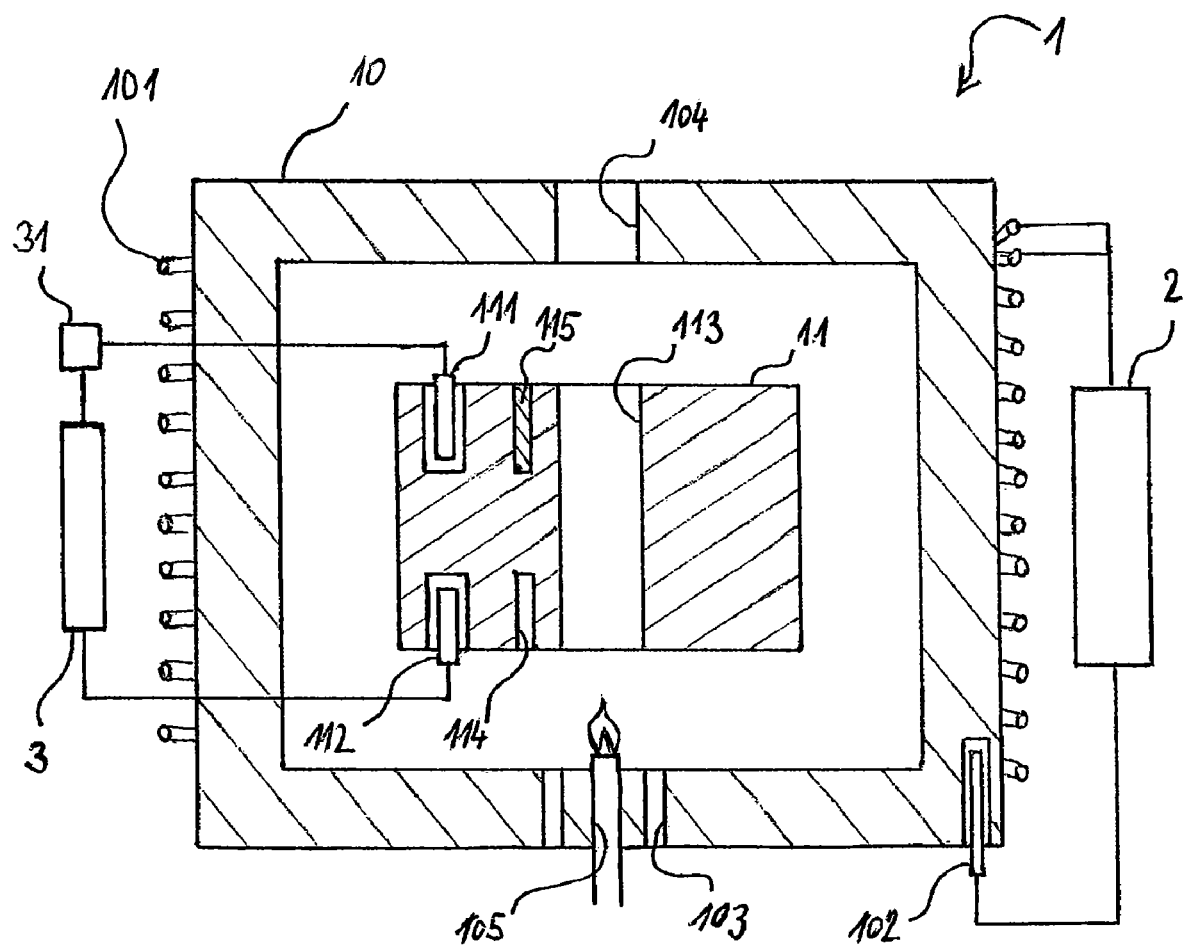
FIG. 1 is the vertical cross-section through the measuring instrument and FIG. 2 is the scheme of the connection of the measuring instrument in the measuring system, with a connection to the pipeline transporting the test gas.
Figure 2:
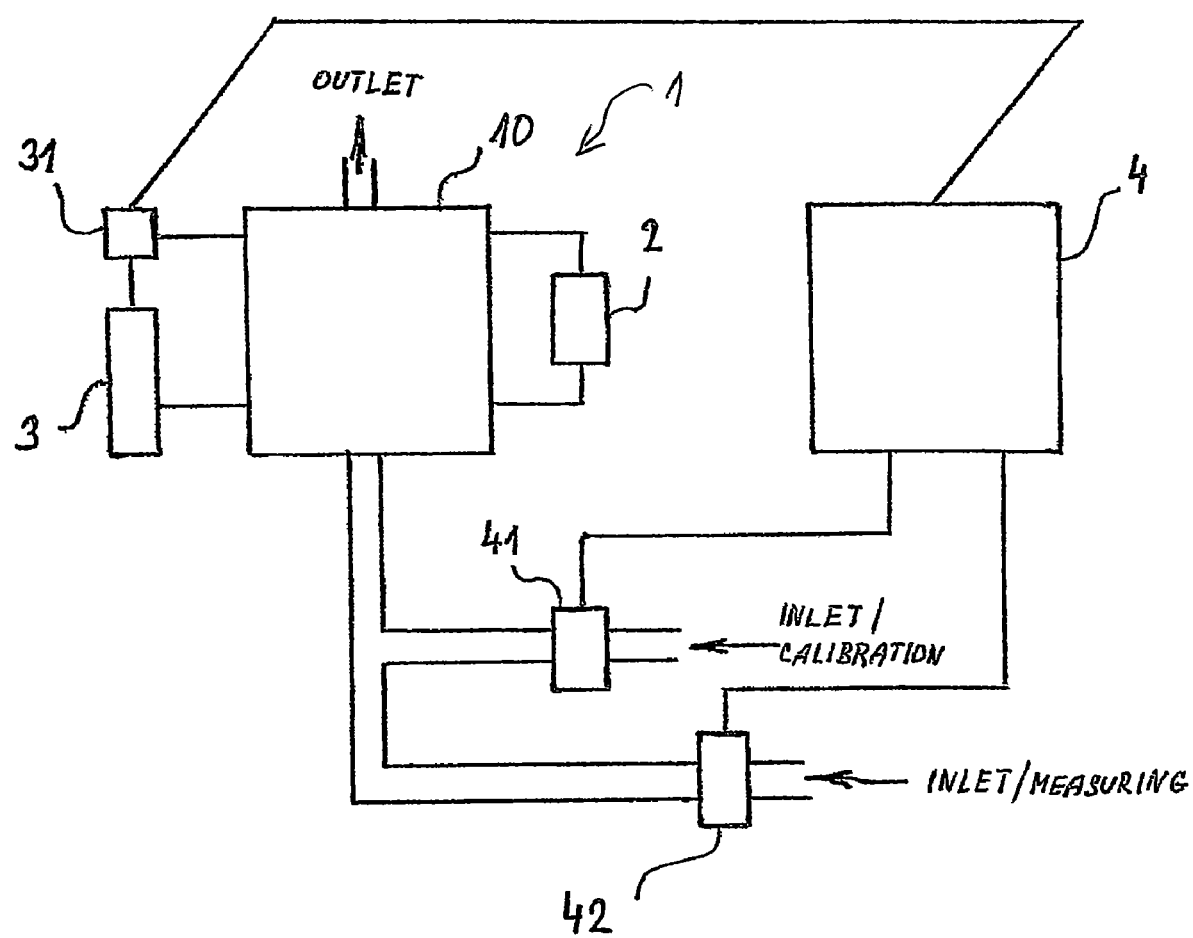

The meter 1 consists of the outer mantle 10 provided with the heating mantle 101, here designed as an electrical resistor heating mantle, with the measuring chamber 11 placed inside the outer mantle 10. The outer mantle 10 is an aluminium cup-shaped case closed with a lid at the bottom. A rather schematic view, represented here as FIG. 1, shows the outer mantle 10 as a closed container, where no separate lid is apparent, but in practice it would be constructed as a case, closed with a lid at the bottom. The bottom lid, or a bottom part, contains the air inlets 103 for air and gas inlets 105 for the test gas or for a calibration gas. The present example has two inlets 103 for introduction of air, perpendicular to the lid plane and between them, in the middle of the lid, there is the gas inlet 105 for introduction of the test or calibration gas, which gas inlet 105 is parallel with the air inlets 103. The outer temperature sensor 102 is placed axially at the bottom edge of the cup-shaped case of the outer mantle 10. The outer temperature sensor 102 is connected to the outer thermostatic apparatus 2 which is further connected to the heating mantle 101. The outer thermostatic apparatus 2 also contains an electric energy source, or can be connected to an external energy source which is not depicted here. The centre of the upper part of the outer mantle 10 contains the outlet 104 for the flue gases, the ratio between the cross-section area of the outlet 104 for the flue gases and the overall cross-section area of the air inlets 103 being 1.3, while the gap between the outer surface of the measuring block 11 and the internal surface of the mantle 10 equals the outer diameter of the measuring block 11. The measuring block 11 is designed as a hollow cylinder made of aluminium, where the axial through-hole 113 in the measuring block 11 has a diameter corresponding to that of the outlet 104 for the flue gases and is directed at the top toward the outlet 104 for the flue gases. In the axial direction, close to the axially directed hole 113, the thermally insulating holes 114 are made in the bottom and top planes of the measuring block 11, while the hole containing the internal temperature sensor 112 is made in the bottom plane in the same direction but closer to the outer circumference of the measuring block 11 and the hole containing the electrical heating block 111 is made in the upper plane. The internal temperature sensor 112 is interconnected with the internal thermostatic apparatus 3 that is further connected, via the measuring apparatus 31 of the electrical input, to the electrical heating block 111. The measuring apparatus 31 is then connected to the evaluating and control unit 4 that is based on a computer and is simultaneously connected to the first dosing unit 41 for the calibration gas and the second dosing unit 42 for the test gas.

The equipment according to the invention operates as follows. First, the calibration stage takes place, i.e., the calibration gas with a precisely known heating capacity, or heating value, is introduced into the meter 1 and is combusted in it, followed by measurement of the temperature at the internal sensor 112 and the storage of the value in the memory of the measuring apparatus, and then the measuring stage takes place, involving introduction of the test gas into the meter 1, its combustion in the meter, with measurement of the electrical input to the electrical heating block 111 by the measuring apparatus and simultaneous maintaining, by the thermostatic apparatus 3, of the temperature of the measuring block 11 measured at the internal sensor 112 at the same value as that determined and stored in the memory during the calibration stage; the value of the heat of combustion of the test gas is then determined from the difference between the value of the heating capacity of the calibration gas and that of the heating capacity of the electrical heating block, while the temperature of the outer mantle 10 is maintained at a constant value, by means of temperature measurement using the outer sensor 102 and subsequent regulation of the heating capacity of the electrical heating block 111, with regulation by the outer thermostatic apparatus 2. The calibration stage is repeated every 30 minutes during the measuring process, while 6 measurements of the heat of combustion value of the test gas are carried out per hour which, in view of the present requirements, can be considered to be continuous measurement. The equipment described above permitted measurements with a precision characterized by deviations not exceeding 1% from the precise value of the heating value verified by laboratory measurements and by control with other calibration gases.

In view of the computer control and monitoring of the measuring process, there is no problem in creating, basically by software means, the so-called thermal fuse which normally closes the gas inlet to heating systems when the gas supply is interrupted, to prevent explosion or pollution by non-ignited gas on resuming the supply. Here an error and alarm signal is generated when the control unit 4 records that the heating capacity of the compensation electrical heating block 111 no longer suffices for the compensation of the decreasing heating capacity of the test gas in the measuring block 11, i.e., that the combustion in the measuring block 11 was actually interrupted. The inlet of gases is then closed and the instrument requires intervention by the personnel.

As far as continuity of measurement is concerned, measurement can be considered continuous, except for the calibration stages. However, these interruptions do not prevent calling the measurement continuous, as the present-day criteria for continuous measurement require that at least 6 measurements be performed per hour. The equipment described here permits at least 6 measurements per hour without any problem, with a calibration frequency of up to every 30 minutes, including the periods of time required for temperature establishment and stabilization in the measuring apparatus 1, after the calibration stages.

INDUSTRIAL APPLICABILITY

The equipment according to the invention can be used for any measurement of the heating value of combustible gases, however, it is especially suitable for continuous, fully automated measurements of the heating value of natural gas and of similar heating gases for which such measurement is required according to the present invoicing regulations. Understandably, the equipment is equally readily applicable to both the substances in the gaseous state that are designated as gases and those designated as vapours.

The invention claimed is:

1. The heating value meter (1) for gases, comprising an outer mantle (10) with thermostatically controlled heating and with at least one air inlet (103) for introduction of air and at least one as inlet (105) for introduction of test gas or for introduction of calibration gas, and a measuring block (11) placed inside the outer mantle (10), characterized in, that outer mantle (10) is cylindrical, it is equipped with a heating mantle (101) on its outer surface and its bottom part contains an outer sensor (102) of an first electrical remote thermometer of the outer thermostatic apparatus (2) placed axially in the wall, and a measuring block (11) is also cylindrical with an axial through-hole (113), it is located coaxially inside the outer mantle (10) and its upper part is equipped with an outlet (104) and an axially inserted internal sensor (112) of a second electrical remote thermometer of the internal thermostatic apparatus (3), while the heating mantle (101) and the outer sensor (102), and also the electrical heating block (111) and the internal sensor (112), are interconnected via the outer and internal thermostatic apparatus (2, 3), adjusted for maintaining of a constant temperature value by regulation of an electrical input to the electrical heating block (111), or of the electrical input to the heating mantle (101), wherein the measuring apparatus (31) of the electrical input of the heating block (111) is connected to an electric lead of the electrical heating block (111).

2. The heating value meter (1) for gases, according to claim 1, characterized in, that the outer mantle (10) and the measuring block (11) are made from a metallic material.

3. The heating value meter (1) for gases, according to claim 1, characterized in, that the outer mantle (10) and the measuring block (11) are made from an alloy based on copper or aluminium.

4. The heating value meter (1) for gases, according to claim 1, characterized in, that a gap exists between the outer surface of the measuring block (11) and the internal surface of the outer mantle (10), wherein a width of the gap equals to 0.3 to 3.0 multiple of the outer diameter of the measuring block (11).

5. The heating value meter (1) for gases, according to claim 1, characterized in, that the overall cross-section area of the outlet (104) for the flue gases equals to 1.1 to 2.0 multiple of the overall cross-section area of the air inlet or inlets (103).

6. The heating value meter (1) for gases, according to claim 1, characterized in, that there are at least two air inlets (103) in the outer mantle (10) and that they are bored at an angle or are diverging from the longitudinal axis of the measuring block (11).

7. The heating value meter (1) for gases, according to claim 1, characterized in, that the electrical heating block (111) and/or the internal sensor (112) are placed in the measuring block (11) closer to its circumference than to its axial through-hole (113).

8. The heating value meter (1) for gases, according to claim 1, characterized in, that a cavity (114) is formed between the position of the electrical heating block (111) and/or the internal sensor (112), and the axial through-hole (113), and/or a shielding body (115) made of a thermally insulating matter is placed in the cavity position.

9. The heating value meter (1) for gases, according to claim 1, characterized in, that the internal thermostatic apparatus (3) is adapted for regulation of the electrical input to the electrical heating block (111), within a range from 5 to 50% of heating input of the calibration gas combusted in the meter (1).

10. The method of operation of the heating value meter (1) constructed according to claim 1, comprising:
performing a calibration operation involving introduction and combustion of a calibration gas with a precisely known heat of combustion in the meter (1);
obtaining a temperature reading at the internal sensor (112) and storing the temperature reading in a memory of the measuring apparatus; and,
introducing and combusting test gas in the meter (1), and simultaneously measuring, by means of the measuring apparatus (31), the electrical input to the electrical heating block (111) and maintaining, by means of the internal thermostatic apparatus (3), the temperature of the measuring block (11) measured at the internal sensor (112), at the same value as that determined and stored in the memory during the calibration step,
wherein the value of the heat of combustion of the test gas is determined from the difference between the heat of combustion value of the calibration gas and the value of heating input of the electrical heating block (111), while keeping the outer mantle (10) temperature constant during the calibration and measuring steps.

11. The method of operation, according to claim 10, characterized in, that the calibration stage is repeated every 30 to 300 minutes.

* * * * *